US00PP25194P2

(12) United States Plant Patent
Luo

(10) Patent No.: US PP25,194 P2
(45) Date of Patent: Dec. 30, 2014

(54) ***MANDEVILLA* PLANT NAMED 'ALEGNUFLOR942'**

(50) Latin Name: *Mandevilla hybrida*
Varietal Denomination: Alegnuflor942

(71) Applicant: Shuming Luo, Dulwich Hill (AU)

(72) Inventor: Shuming Luo, Dulwich Hill (AU)

(73) Assignee: Nuflora International Pty. Ltd., Macquarie Fields, New South Wales (AU)

( * ) Notice: Subject to any disclaimer, the term of this patent is extended or adjusted under 35 U.S.C. 154(b) by 81 days.

(21) Appl. No.: 13/815,334

(22) Filed: Feb. 21, 2013

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Annette Para
(74) *Attorney, Agent, or Firm* — C. A. Whealy

(57) ABSTRACT

A new and distinct cultivar of *Mandevilla* plant named 'Alegnuflor942', characterized by its upright and somewhat vining to climbing plant habit; moderately vigorous growth habit; early and freely flowering habit; long flowering period; dark red-colored flowers; and good garden performance.

1 Drawing Sheet

Botanical designation: *Mandevilla hybrida.*
Cultivar denomination: 'ALEGNUFLOR942'.

BACKGROUND OF THE INVENTION

The present invention relates to a new and distinct cultivar of *Mandevilla* plant, botanically known as *Mandevilla hybrida* and hereinafter referred to by the name 'Alegnuflor942'.

The new *Mandevilla* plant is a product of a planned breeding program conducted by the Inventor in Cobbitty, New South Wales, Australia. The objective of the breeding program is to create new *Mandevilla* plants with large attractive flowers and are temperature-tolerant and tolerant to pathogens and pests common to *Mandevilla* plants.

The new *Mandevilla* plant originated from a cross-pollination made by the Inventor in Cobbitty, New South Wales, Australia in January, 2006 of a proprietary selection of *Mandevilla hybrida* identified as code number X03.2.8, not patented, as the female, or seed parent with a proprietary selection of *Mandevilla hybrida* identified as code number X03.2.2, not patented, as the male, or pollen, parent. The new *Mandevilla* plant was discovered and selected by the Inventor as a single flowering plant from within the progeny of the stated cross-pollination in a controlled greenhouse environment in Cobbitty, New South Wales, Australia in December, 2009.

Asexual reproduction of the new *Mandevilla* plant by cuttings in Macquarie Fields, New South Wales, Australia since January, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Alegnuflor942'. These characteristics in combination distinguish 'Alegnuflor942' as a new and distinct *Mandevilla* plant:

1. Upright and somewhat vining to climbing plant habit.
2. Moderately vigorous growth habit.
3. Early and freely flowering habit.
4. Long flowering period.
5. Dark red-colored flowers.
6. Good garden performance.

Plants of the new *Mandevilla* can be compared to plants of the female parent selection. Plants of the new *Mandevilla* differ primarily from plants of the female parent selection in the following characteristics:

1. Plants of the new *Mandevilla* are not as strongly vining as plants of the female parent selection.
2. Plants of the new *Mandevilla* have smaller flowers than plants of the female parent selection.
3. Plants of the new *Mandevilla* and the female parent selection differ in flower color as plants of the female parent selection have burgundy-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* have smaller flowers than plants of the male parent selection.
2. Plants of the new *Mandevilla* and the male parent selection differ in flower color as plants of the male parent selection have lighter red-colored flowers.

Plants of the new *Mandevilla* can be compared to plants of *Mandevilla hybrida* 'Rio Red', not patented. In side-by-side comparisons conducted in Cobbitty, New South Wales, Australia, plants of the new *Mandevilla* differed primarily from plants of 'Rio Red' in the following characteristics:

1. Plants of the new *Mandevilla* were more vigorous than plants of 'Rio Red'.

2. Plants of the new *Mandevilla* had slightly smaller flowers than plants of 'Rio Red'.
3. Plants of the new *Mandevilla* and 'Rio Red' differed in flower color as plants of 'Rio Red' had lighter red-colored flowers.

Plants of the new *Mandevilla* can be compared to plants of *Mandevilla hybrida* 'Pretty Red', not patented. In side-by-side comparisons conducted in Cobbitty, New South Wales, Australia, plants of the new *Mandevilla* differed primarily from plants of 'Pretty Red' in the following characteristics:

1. Plants of the new *Mandevilla* were not as vining as plants of 'Pretty Red'.
2. Plants of the new *Mandevilla* had thicker leaves than plants of 'Pretty Red'.
3. Plants of the new *Mandevilla* had smaller flowers than plants of 'Pretty Red'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the following detailed botanical description which accurately describe the actual colors of the new *Mandevilla* plant.

The photograph at the top of the sheet comprises a side perspective view of a typical flowering plant of 'Alegnuflor942' grown in a container.

The photograph at the bottom of the sheet is a close-up views of a typical flowering plants of 'Alegnuflor942'.

DETAILED BOTANICAL DESCRIPTION

The aforementioned photographs and following observations, measurements and values describe plants grown in one-gallon containers during the summer and early autumn in a polyethylene-covered greenhouse in Vista, Calif. and under cultural practices typical of commercial *Mandevilla* production. During the production of the plants, day temperatures averaged 29° C. and night temperatures averaged 21° C. Plants were pinched two times and were 20 weeks old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Alegnuflor942'.

Parentage:

*Female, or seed, parent*.—Proprietary selection of *Mandevilla hybrida* identified as code number X03.2.8, not patented.

*Male, or pollen, parent*.—Proprietary selection of *Mandevilla hybrida* identified as code number X03.2.2, not patented.

Propagation:

*Type*.—By cuttings.

*Time to initiate roots, summer*.—About ten days at 25° C. to 30° C.

*Time to initiate roots, winter*.—About 16 days at 15° C. to 20° C.

*Time to produce a rooted young plant, summer*.—About four weeks at 25° C. to 30° C.

*Time to produce a rooted young plant, winter*.—About six weeks at 15° C. to 20° C.

*Root description*.—Medium in thickness, fibrous; white in color becoming creamy white to golden with development.

*Rooting habit*.—Freely branching; dense.

Plant description:

*Plant and growth habit*.—Upright and somewhat vining to climbing plant habit; moderately vigorous growth habit; and moderate growth rate.

*Plant height*.—About 44 cm.

*Plant diameter*.—About 32 cm by 36 cm.

*Lateral branch description*.—Branching habit: Moderate branching habit; pinching enhances lateral branch development; about five primary lateral branches each with numerous secondary branches. Length: About 34 cm. Diameter: About 3 mm. Internode length: About 3 cm. Texture: Smooth, glabrous; becoming woody with development. Color: Close to 146B; color becoming closer to 199B with development.

Foliage description:

*Arrangement*.—Opposite, simple.

*Length*.—About 7.2 cm.

*Width*.—About 4.6 cm.

*Shape*.—Elliptic to oval.

*Apex*.—Acuminate.

*Base*.—Equilateral to slightly cordate.

*Margin*.—Entire.

*Texture, upper and lower surfaces*.—Smooth, glabrous; leathery.

*Venation pattern*.—Pinnate, arcuate.

*Color*.—Developing leaves, upper and lower surfaces: Close to 146B. Fully expanded leaves, upper surface: Close to N137B; venation, close to 147B. Fully expanded leaves, lower surface: Close to 146A; venation, close to 146D.

*Petioles*.—Length: About 2 cm. Diameter: About 2 mm. Texture, upper and lower surfaces: Smooth, glabrous. Color, upper surface: Close to 146C. Color, lower surface: Close to 146D.

Flower description:

*Flower type and habit*.—Salverform flowers arranged alternately in axillary clusters similar to racemes; flowers face horizontally to slightly drooping; freely flowering habit, about five to seven flowers and flower buds per cluster and about 40 flowers developing per plant.

*Natural flowering season*.—Early flowering habit, plants begin flowering about six to eight weeks after planting; long flowering period, plants flower continuously from spring into the autumn in Southern California.

*Flower longevity on the plant*.—About five days; flowers not persistent.

*Fragrance*.—None detected.

*Flower buds*.—Height: About 7 cm. Diameter: About 1 cm. Shape: Elongated oblong. Color: Close to 59C.

*Cluster height*.—About 11.2 cm.

*Cluster diameter*.—About 5.5 cm by 8 cm.

*Flower diameter*.—About 6.2 cm.

*Flower depth (length)*.—About 7.4 cm.

*Flower throat diameter*.—About 1.5 cm.

*Flower tube length*.—About 6 cm.

*Flower tube diameter, base*.—About 5 mm.

*Corolla*.—Arrangement and appearance: Single whorl of five petals, petals not imbricate; lobes asymmetrical giving a pinwheel appearance to the flower. Petal lobe length: About 2.7 cm. Petal lobe width: About 2.4 cm. Petal lobe shape: Asymmetrical. Petal apex: Acuminate. Petal margin: Entire. Petal texture, upper and lower surfaces: Smooth, glabrous; velvety. Throat texture: Smooth, glabrous. Tube texture: Smooth, glabrous. Color: Petal lobe, when opening, upper surface: Close to 53A. Petal lobe, when opening, lower surface: Close to 60A. Petal lobe, fully opened, upper surface: Close to 53A; towards the apex, darker than 53A; venation, close to 53A; color does not fade with development. Petal lobe, fully opened, lower surface: Close to 53A to 53B; venation, close to 53B. Throat: Close to 26B; venation, close to 26B. Tube: Close to 53C; towards the base, close to 145D; base, close to 145B to 145C; venation, close to 53C.

*Sepals*.—Arrangement and appearance: Five per flower fused in a single whorl; calyx short funnelform and five-pointed. Length: About 8 mm. Width: About 1.5 mm. Shape: Lanceolate. Apex: Acute to acuminate. Margin: Entire. Texture, upper and lower surfaces: Smooth, glabrous. Color, upper and lower surfaces: Close to 145C.

*Peduncles*.—Length: About 3.6 cm. Diameter: About 1.5 mm. Texture: Smooth, glabrous. Strength: Strong, flexible. Aspect: About 35° to 45° from lateral branch axis. Color: Close to 144A.

*Pedicels*.—Length: About 1.4 cm to 1.7 cm. Diameter: About 2 mm. Texture: Smooth, glabrous. Strength: Strong, flexible. Aspect: About 25° to 30° from peduncle axis. Color: Close to 145A.

*Reproductive organs*.—Stamens: Quantity per flower: Typically five. Filament length: About 5 mm. Filament color: Close to NN155A. Anther length: About 1 cm. Anther shape: Lanceolate. Anther color: Close to 158B. Pollen amount: Scarce. Pollen color: Close to NN155A. Pistils: Quantity per flower: Typically one. Pistil length: About 2.7 cm. Style length: About 2.2 cm. Style color: Close to 145D. Stigma shape: Rounded; five-lobed. Stigma color: Close to 144C. Ovary color: Close to 146D.

*Seeds and fruits*.—Seed and fruit production has not been observed on plants of the new *Mandevilla*.

Disease & pest tolerance: Plants of the new *Mandevilla* have been observed to be somewhat tolerant to mites. Plants of the new *Mandevilla* have not been noted to be resistant to pathogens and other pests common to *Mandevilla* plants.

Garden performance: Plants of the new *Mandevilla* have been observed to have good garden performance and to tolerate rain, wind, full sunlight and temperatures from about 5° C. to about 45° C.

It is claimed:

1. A new and distinct *Mandevilla* plant named 'Alegnuflor942' as illustrated and described.

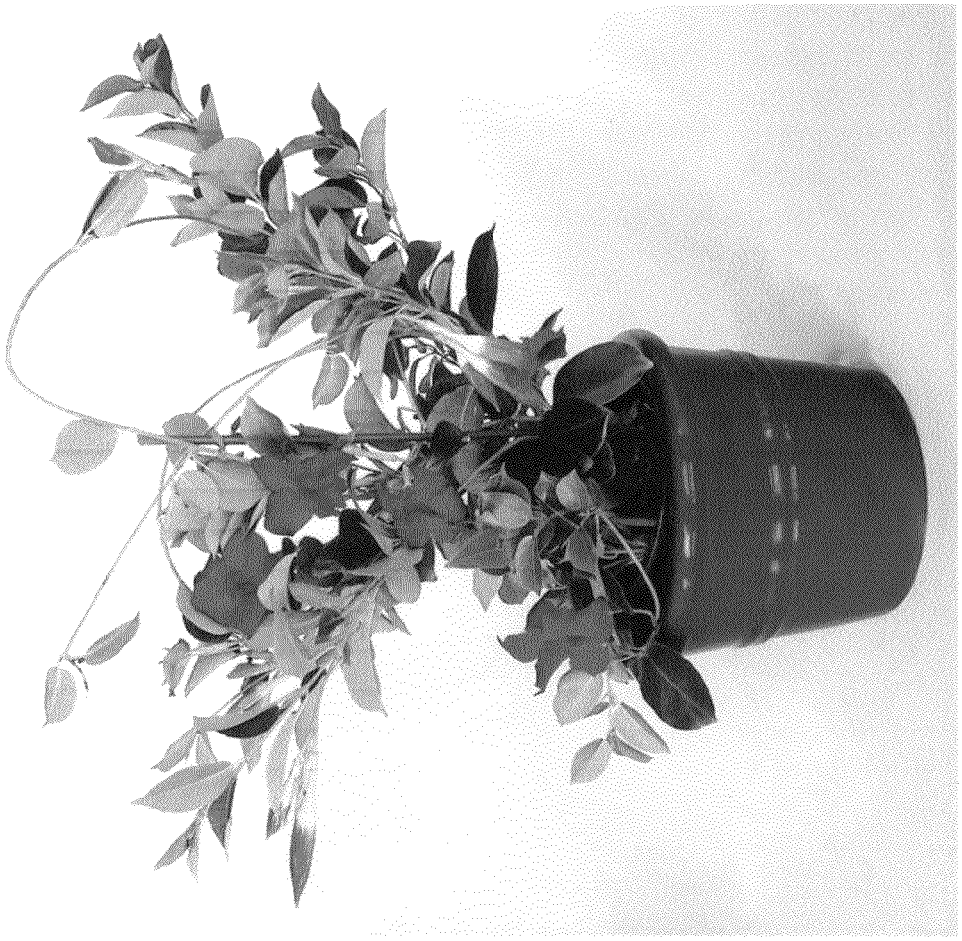
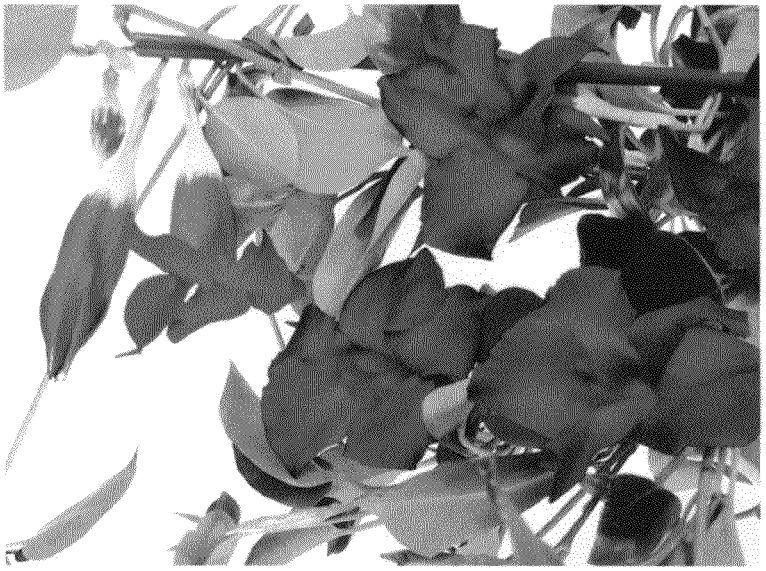

* * * * *